(12) United States Patent
Pattekar et al.

(10) Patent No.: US 10,839,957 B2
(45) Date of Patent: Nov. 17, 2020

(54) COMPUTER-IMPLEMENTED SYSTEM AND METHOD FOR TRACKING ENTITY LOCATIONS AND GENERATING HISTORIES FROM THE LOCATIONS

(71) Applicant: Palo Alto Research Center Incorporated, Palo Alto, CA (US)

(72) Inventors: Ashish V. Pattekar, Cupertino, CA (US); Christopher L. Chua, San Jose, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 470 days.

(21) Appl. No.: 14/262,642

(22) Filed: Apr. 25, 2014

(65) Prior Publication Data
US 2015/0310180 A1    Oct. 29, 2015

(51) Int. Cl.
*G16H 40/20*    (2018.01)

(52) U.S. Cl.
CPC .................................. *G16H 40/20* (2018.01)

(58) Field of Classification Search
CPC ........ G06Q 10/00; G06Q 50/00; G16H 10/00; G16H 15/00; G16H 20/00; G16H 30/00; G16H 40/00; G16H 50/00; G16H 70/00; G16H 80/00; G16H 10/40; G16H 20/10; G16H 20/13; G16H 20/17; G16H 40/20
USPC .................................................. 705/2, 3, 20
See application file for complete search history.

(56) References Cited

U.S. PATENT DOCUMENTS

| 2002/0111826 | A1  | 8/2002  | Potter et al. |
| 2002/0133379 | A1  | 9/2002  | Lewis |
| 2003/0016122 | A1  | 1/2003  | Petrick |
| 2008/0059230 | A1  | 3/2008  | Manning |
| 2009/0171939 | A1* | 7/2009  | Athsani ............. G06F 17/30241 |
| 2012/0173257 | A1* | 7/2012  | Preiss .................... G06Q 10/06 705/2 |
| 2012/0203785 | A1  | 8/2012  | Awada |
| 2012/0266102 | A1* | 10/2012 | Dempski ................... G06F 8/65 715/781 |
| 2013/0314210 | A1  | 11/2013 | Schoner |
| 2014/0035726 | A1  | 2/2014  | Schoner |
| 2014/0162692 | A1* | 6/2014  | Li .......................... H04L 67/40 455/456.3 |

(Continued)

*Primary Examiner* — Robert W Morgan
*Assistant Examiner* — Charles P Coleman
(74) *Attorney, Agent, or Firm* — Krista A. Wittman

(57) ABSTRACT

A computer-implemented system and method for tracking entity locations and generating histories from the locations is provided. A tracker is associated with identification data for an entity and placed with the entity. A location of the tracker is determined. Three or more reader systems that receive location readings from the tracker are identified. A reading range of each of the reader systems is determined. An overlapping interrogation zone having a region that is shared by the reading ranges of the reader systems is located. The location of the tracker is calculated based on the overlapping zone. The location and an associated time stamp are stored on a central server with other locations of the tracker and time stamps obtained over time. A request is received for a location history of the entity. A portion of the locations are collected from the central database for the tracker as the location history.

14 Claims, 17 Drawing Sheets

(56) References Cited

U.S. PATENT DOCUMENTS

| | | | |
|---|---|---|---|
| 2015/0169915 A1* | 6/2015 | Petre | G06K 19/0702 340/10.6 |
| 2015/0195315 A1* | 7/2015 | Kidron | G06F 17/30743 709/219 |
| 2015/0213206 A1* | 7/2015 | Amarasingham | G06F 19/327 705/2 |
| 2015/0213225 A1 | 7/2015 | Amarasingham | |
| 2015/0278765 A1* | 10/2015 | Dantuluri | G06Q 10/109 705/319 |

* cited by examiner

180

Entity: Julie Smith     *3472
Occupation: Doctor
Security Access: All
Date(s): December 27, 2013

| Time | Location |
|---|---|
| 12:15 pm | Staff locker room |
| 12:30 | Hall outside Room 333 W |
| 12:45 | Washroom in surgery 3A W |
| 1:00 | Surgery 3A W |
| 1:15 | |
| 1:30 | |
| 1:45 | |
| 2:00 | |
| 2:15 | Surgery 3A W |

FIG. 17

COMPUTER-IMPLEMENTED SYSTEM AND METHOD FOR TRACKING ENTITY LOCATIONS AND GENERATING HISTORIES FROM THE LOCATIONS

FIELD

This application relates in general to tracking objects and, in particular, to a computer-implemented system and method for tracking entity locations and generating histories from the locations.

BACKGROUND

Most hospitals are large organizations that provide medical care and treatment to numerous patients. For example, in 2010, 35.1 million individuals were admitted to non-Federal short-stay hospitals in the U.S and the average stay was 4.8 days. To ensure proper patient care, each hospital must employ large numbers of individuals and maintain adequate types and numbers of medical equipment. Working in a hospital can be chaotic due to the nature of patient care, but can be further intensified by challenges stemming from the extreme numbers of employees, patients, and equipment that must be maintained and monitored.

The challenges can include locating medical equipment, finding a particular employee, and tracking patients. For example, some medical equipment, such as IV pumps and defibrillators are used by multiple patients, on an as needed basis. Some hospitals designate a single defibrillator for each floor, and if the defibrillator is in use while a different patient on the same floor goes into ventricular fibrillation, another defibrillator must be obtained quickly and brought to the patient to prevent brain damage and possibly death. However, doctors and nurses are often unaware whether a defibrillator is in use and may only find out by physically going to the machine. The time spent looking for an available piece of critical equipment such as a defibrillator must be minimized to reduce damage to the patient and ensure high care quality.

With respect to employees, a doctor or other caretaker can be paged when needed for a medical emergency. However, if occupied, the doctor may not immediately respond to the page and must be located. Time spent looking for a doctor or other medical professional to attend to the emergency can be detrimental to the health of a patient and the outcome of the emergency. In addition to employees, a hospital must monitor patients to provide treatment and ensure patient safety. For example, measures must be taken to prevent newborn babies from being mistakenly switched or abducted from the hospital. In a further example, patients sometimes leave the hospital on their own before finishing treatment or being formally discharged and alerting the hospital staff when such a situation comes up may be of value if an intervention can be made to avoid the situation of a patient leaving the hospital before completing treatment There are existing approaches and equipment that assist hospitals monitor equipment, employees, and patients. For example, medical equipment can be maintained using bar codes. A unique bar code is attached to each piece of medical equipment and the bar code is stored in a database with information about the medical equipment. However, use of bar codes only allows a user to look up information about the corresponding piece of equipment, such as when the equipment was last used or serviced, and fails to provide a location of the equipment. Infrared technology can be used to observe people; however, a direct line of sight is needed, making the implementation of the infrared technology expensive and complex. Further, RFID tags are often attached to babies via ankle bracelets and the tags are detected by monitors positioned throughout the hospital. Yet, using a single RFID reader to detect an individual or object can, by itself, only determine the presence or absence of that individual or object, not its precise real time location and movement.

Therefore, there is a need for identifying real-time locations of medical personnel, patients, hospital visitors and equipment that is efficient and of reasonable cost. Moreover, the real-time locations should be stored in a database that can be queried later on in order to determine a location history.

SUMMARY

A user can efficiently locate an entity within a hospital using a locator system that employs a tracker, such as an RFID tag. A unique tracker is obtained and physically associated with a particular entity by affixing the tracker to the entity. Further, the tracker identification (ID) information such a unique ID number is entered into a database with identifying information regarding the entity such that appropriate association between the location of the tracker and the entity being tracked can be made once the locator system is in use.

The locator system includes an array of RFID reader systems placed in strategically located nodes throughout the hospital. The nodes are located so the interrogation range of individual RFID reader systems overlap that of neighboring nodes. The location of an identified RFID tag can then be determined by a basic triangulation method, or by correlating the signal strengths of different reader systems located at different nodes for more precise location identification. RFID reader systems with tunable ranges can be used to improve accuracy and reduce the number of nodes needed. In one example, sweeping through the tunable range by modulating the radio frequency (RF) power emitted by an antenna associated with the reader and progressively identifying the tags that come into range could be used to pinpoint the location of specific tags and corresponding vehicles. In another embodiment, the signal strength associated with individual tags could be used to estimate distance from a given reader node by looking up previously calibrated information on signal strength and distance from a particular node, and thereby, improve the location tracking accuracy in addition to basic triangulation methods.

Readings by the reader systems are obtained to determine real time entity locations and movement, which are then stored in the database. Subsequently, when a user needs to locate an entity, the user can access a user interface on a display such as a TV screen, computer screen, smartphone or smartwatch and/or tablet computer screen, and enter an identifier for the entity. The locator system then provides a location of the entity to the user. The location can be obtained from the database or can be determined upon the location request.

A further embodiment provides a computer-implemented system and method for tracking entity locations and generating histories from the locations. A tracker is associated with identification data for an entity and placed with the entity. A location of the tracker is determined. Three or more reader systems that receive location readings from the tracker are identified. A reading range of each of the reader systems is determined. An overlapping interrogation zone having a region that is shared by the reading ranges of the reader systems is located. The location of the tracker is calculated based on the overlapping interrogation zone. The location and a corresponding time stamp are stored on a central server with other locations of the tracker and time stamps obtained over time. A request is received for a location history of the entity. A portion of the locations is collected from the central database for the tracker as the location history, which is provided in reply to the request.

Still other embodiments of the present invention will become readily apparent to those skilled in the art from the following detailed description, wherein is described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

BRIEF DESCRIPTION OF THE DRAWINGS

FIG. 17 is a block diagram showing, by way of example, a chart for a location history.

DETAILED DESCRIPTION

When a medical emergency occurs in a hospital, quickly locating appropriate individuals and equipment needed to treat the emergency is crucial to prevent further medical complications. Conventional methods for monitoring entities, such as people and equipment, fail to provide real-time locations and can still require a user to spend significant time and energy locating the needed entity. The time spent searching for an entity can result in decreased efficiency, increased costs, and avoidable medical complications. Assisting a user to quickly and easily find people or equipment within a hospital can reduce the time spent searching for an entity, which can increase hospital efficiency, while decreasing a number of medical complications and costs.

Figure 1:
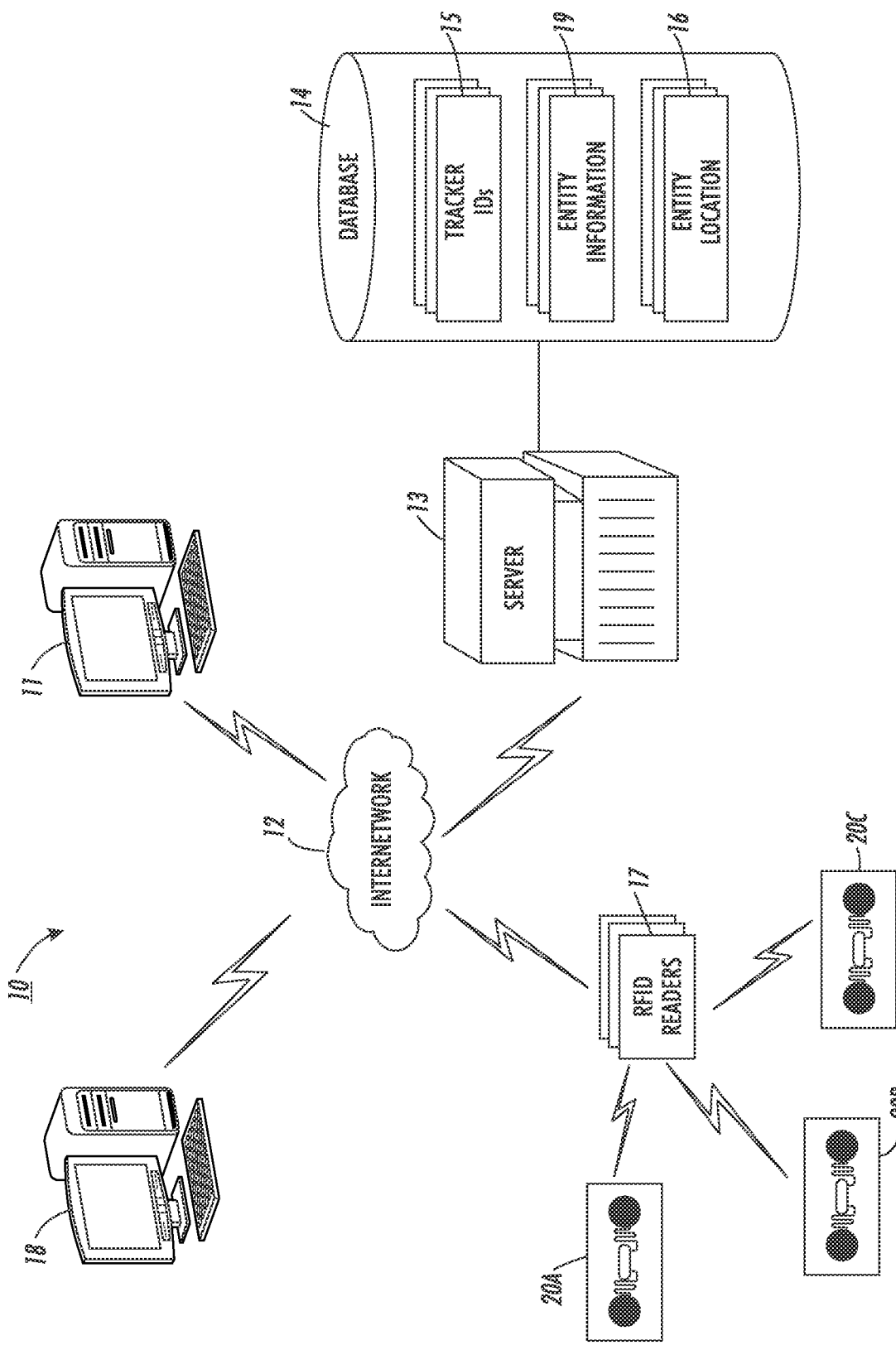
FIG. 1 is a block diagram showing a computer-implemented system for tracking entity locations and generating histories from the locations, in accordance with one embodiment.

Tracking people and equipment helps to quickly locate people and equipment when needed. FIG. 1 is a block diagram showing a computer-implemented system 10 for tracking entity locations and determining histories from the locations, in accordance with one embodiment. A tracker 20a-c is assigned to an entity (not shown) located within a hospital and an identity 15 of the tracker 20a-c is entered into a computer 11 for transmitting to a server 13 via an internetwork 12, such as the Internet or a local area network (LAN), including a wired Ethernet or a wireless (WiFi) network, and storing in a database 14 with identifying information 19 for the entity. The entity can include an individual, such as a hospital employee or patient, or medical equipment, as well as other types of entities. Meanwhile, the tracker 20a-c can be disposable or reusable, and can be associated with an entity via an adhesive, a lanyard, a wrist or leg band, and a clip, as well as by other means. The trackers 20a-c are further discussed below with reference to FIGS. 3-6.

Reader systems that can identify the trackers, such as through radio frequency identification, are dispersed throughout the hospital and can be affixed to walls and ceilings of the building. The reader systems can be placed in strategically located nodes within the hospital and can use RFID technology to determine an entity's location. In one embodiment, the nodes are located so the interrogation range of individual RFID reader systems overlaps that of neighboring nodes. The location of an identified RFID tag can then be determined by a basic triangulation method, or by correlating the signal strengths of different reader systems located at different nodes for more precise location identification. Placement of the nodes is further described below with reference to FIGS. 8-12.

Once the tracker 20a-c is associated with an entity, the reader systems can search for and identify the tracker 20a-c within range on a periodic, continual, or as requested interrogation basis as the entity moves throughout the hospital. The reader systems that identify the tracker at each interrogation are noted and a location of the entity is determined based on the reader systems that identify the tracker, the location of the reader systems, and the range of the reader systems. Once determined, the tracker locations are stored in the database 14 with the time of interrogation for providing to a user as the entity location, upon request. The tracker locations can also be stored in a separate database. In a further embodiment, the tracker location can be determined upon request by the user. Determining tracker and entity location is further discussed below with reference to FIG. 9.

To obtain the entity location, the user can enter a request in a computer 10, 18, tablet (not shown), or mobile computing device (not shown), as well as any other device that can be interconnected to the server 13 and database 14 via the internetwork 12. The computers 10, 18 can be located throughout the hospital, with at least one computer located on every floor, such as at a nurse's station. Alternatively, or in addition to the computers, doctors, nurses and other hospital employees can utilize tablets or mobile computing devices to look up an entity location.

Figure 2:
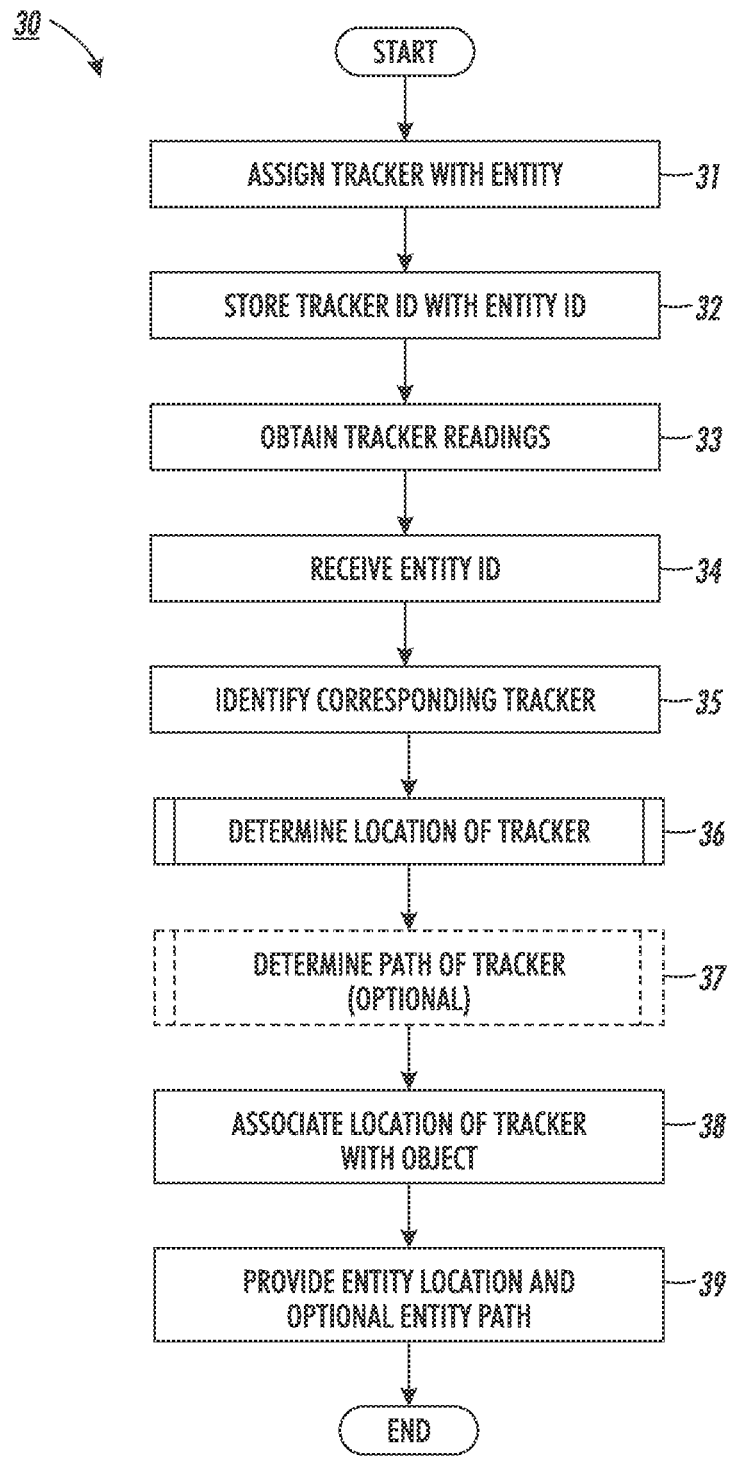
FIG. 2 is a flow diagram showing a method for tracking entity locations and generating histories from the locations, in accordance with one embodiment.

The entity location tracking system assists a user in finding entities that are difficult to locate within the hospital. FIG. 2 is a flow diagram showing a computer-implemented method 30 for tracking entity locations and generating histories from the locations, in accordance with one embodiment. A tracker is assigned to an entity (step 31) to be tracked, including equipment or people within the hospital, including doctors, nurses, other employees, patients, and visitors, as well as other types of entities to be tracked within the hospital. The trackers can be assigned to the entities randomly, in consecutive order, or by an employee of the hospital or a third party. Subsequently, the tracker is conjoined with the entity based on the entity type. The tracker can be directly affixed to objects, such as furniture or equipment, or indirectly associated with people via a lanyard, clip, or bracelet. For example, a tracker printed onto an adhesive sticker can be directly provided on a piece of medical equipment, while patients may wear the tracker on a wrist band or ankle band, and doctors can wear the tracker around their neck on a lanyard.

An identifier of the tracker is entered into a database with identification information for the entity (step 32). The entity identification information can vary based on a type of entity. For example, patient entity information can include name, hospital room, and doctor, while visitor entities can include type of visitor and authorized or unauthorized access to particular areas of the hospital, and equipment can include model number, make, and year of production. Other types of information are possible.

Once the tracker is associated with the entity, one or more reader systems located throughout the hospital can obtain readings (step 33) from the tracker based on a location of the tracker. Interrogation of the reader systems can occur at various times, such as on a periodic, continual, or as-requested basis. During each interrogation, readings from the reader systems that identified the tracker can be processed to determine a location of the entity. The location of the entity can be based on the reader systems that identified the tracker, a reading range of those reader systems, and a location of those reader systems. For instance, a triangulation method can be applied to the data to identify an approximate location or area in a vicinity of location of the entity by identifying overlapping zones of the ranges of the reader nodes that are able to successfully communicate with the tracker. Alternatively, relative signals from the reader nodes that identify the tracker can be used to determine the tracker position, and thus, entity location within the hospital, in a more accurate fashion. Readers receiving a stronger signal are closer to the tracker than readers receiving weaker signals. Information on which overlapping reader nodes are within range of the tracker can only determine whether the tracker is inside the overlap region. The relative strengths of received signals provide an extra dimension for triangulating the precise location of the tracker within the overlap region. Determining a location of the entity is further discussed below in detail with reference to FIGS. 8-12.

When a user needs to quickly locate an entity, or obtain a past location or location history for the entity, the user can enter identifying information (step 34) for the entity into a computer. The identifying information can include, inter alia, a name, identification number, make and model, or date of birth, as well as other types of information. Upon receipt by the computer, the identifying information is transmitted to the server for identifying the associated entity and for determining the tracker (step 35) associated with the entity. If requested, a current or past location of the entity is obtained (block 36). A current location can be determined upon receipt of the request or alternatively, a most recent location for the entity, which is stored in a database, can be used as the current location. When determined upon request, the reader systems are polled to identify those reader systems that obtain readings from the tracker. Information regarding the reader systems that identify the tracker is processed to determine a location of the tracker, such as by triangulation, as described above with respect to FIG. 1.

Further, if a location history for the entity is optionally requested, a path of the tracker associated with the entity is generated (step 37) based on the current and past locations for that tracker within a specified range of time. The time range for the history can range from hours, to days, to months, and to years. Other time ranges are possible. Once determined, the location of the tracker is designated as a location of the entity (block 38) and provided to the user (block 39), along with the history, if requested.

The entity location is determined as a location of the tracker so the entity and tracker must be closely associated. The type of association between the entities and trackers can depend on a type of the entity, as described below with reference to FIGS. 3-6. Further, a type of tracker to be associated with an entity is also dependent on the entity type. For example, patients temporarily reside at a hospital, while employees are located at the hospital on a regular and generally, long term basis. Thus, disposable trackers can be provided to the patients, while reusable trackers can be provided to employees. The disposable trackers can be embedded in a disposable wrist or ankle band for attaching to a patient during the patient's hospital stay. Additionally, active tags can be used for doctors to more accurately determine a location of doctor needed for an emergency, while passive tags can be used for equipment or patients to determine a vicinity or region within which the entity is located.

Figure 3:
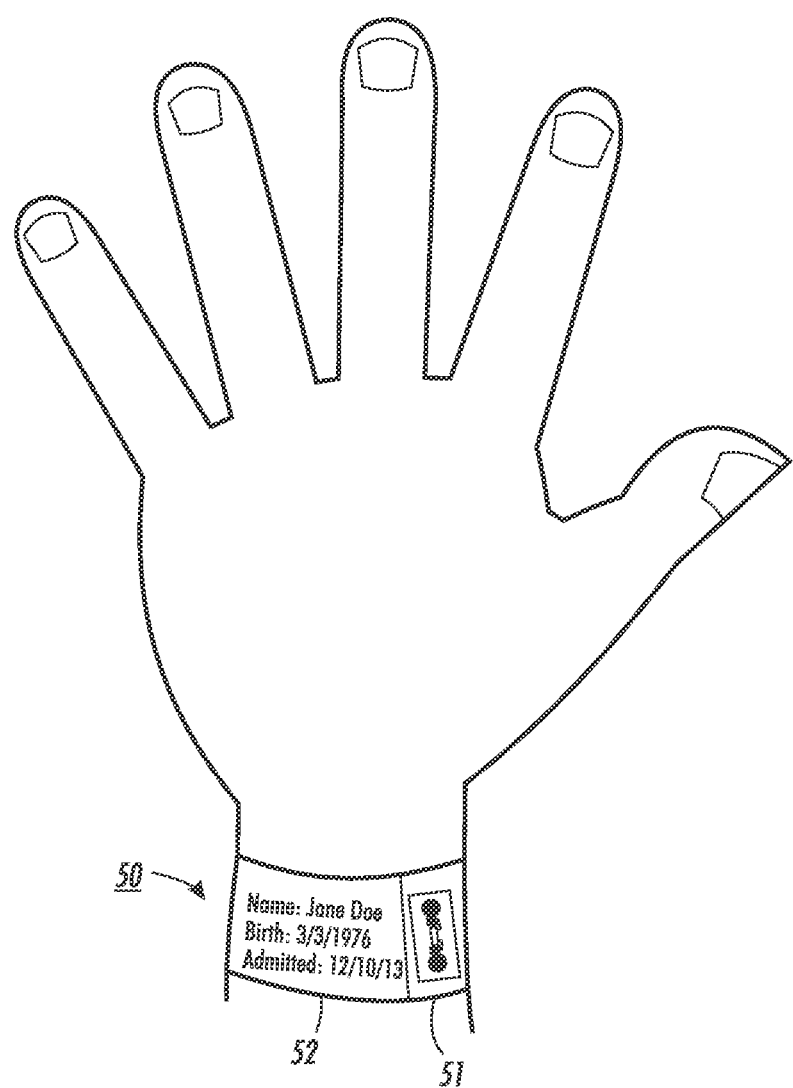
FIG. 3 is a block diagram showing, by way of example, a wristband with a tracker.

The trackers can be assigned and conjoined with the entities upon entry into the hospital; however, other times are possible. Generally, when a patient is admitted to a hospital, a band with identifying information is wrapped around the patient's wrist or ankle, and the tracker can be incorporated into the identification band itself. FIG. 3 is a block diagram showing, by way of example, a wristband with a tracker. The wristband 50 can include a bracelet or strap that is secured around an individual's wrist. The tracker 51 can be printed directly on the wristband 50, embedded within the wristband, or can be removably affixed, such as by adhesive, glue, or rubber. As well, the bracelet can be made from plastic, vinyl, cloth, paper, or other materials, including Tyvek. Ankle bands can be made from the same material as the wristbands or from separate material, and the tracker can be printed directly on, embedded in, or removably affixed to the ankle band.

As described above, the wrist and ankle bands can include identifying information 52, such as the patient name, birth date, and admission date. Other types of identifying information are possible, including a baby's name, allergies, and room number. Upon admittance of a patient, a band embedded with a tracker can be printed with the patient's identifying information. However, if not embedded, the tracker can be printed with the identifying information or a pre-printed tracker can be affixed to the band. The band is then applied to the patient for wear during the patient's stay. When the patient is discharged, the band is removed and disposed of for sanitation purposes.

Figure 4:
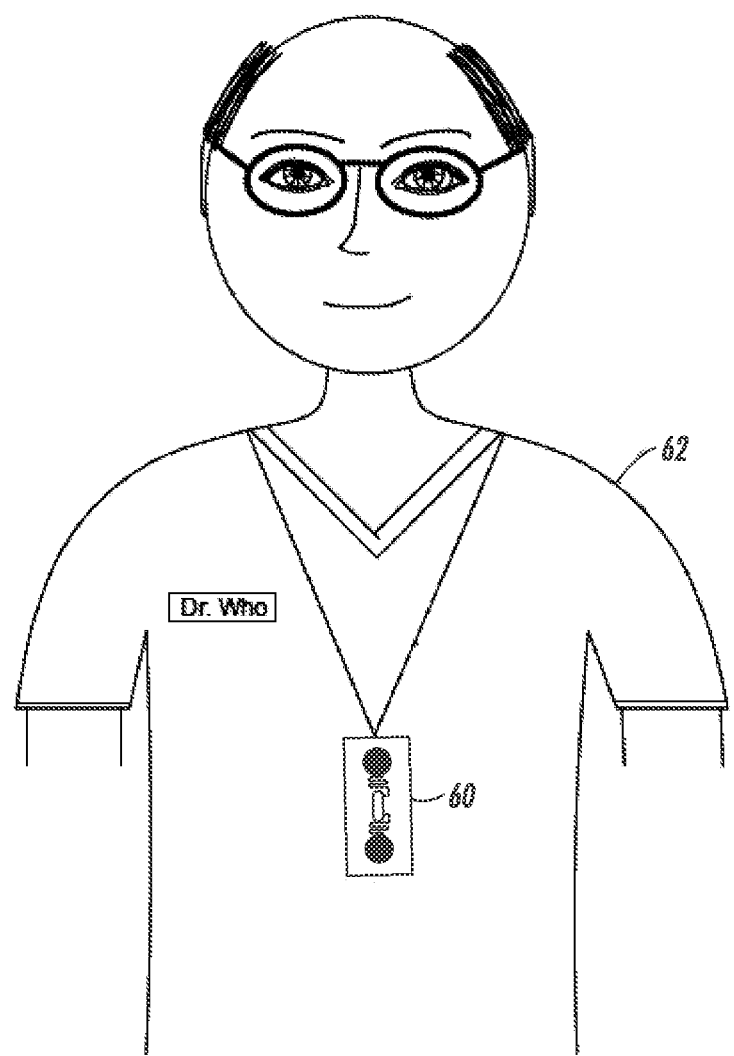
FIG. 4 is a block diagram showing, by way of example, a tracker on a lanyard.
Figure 5:
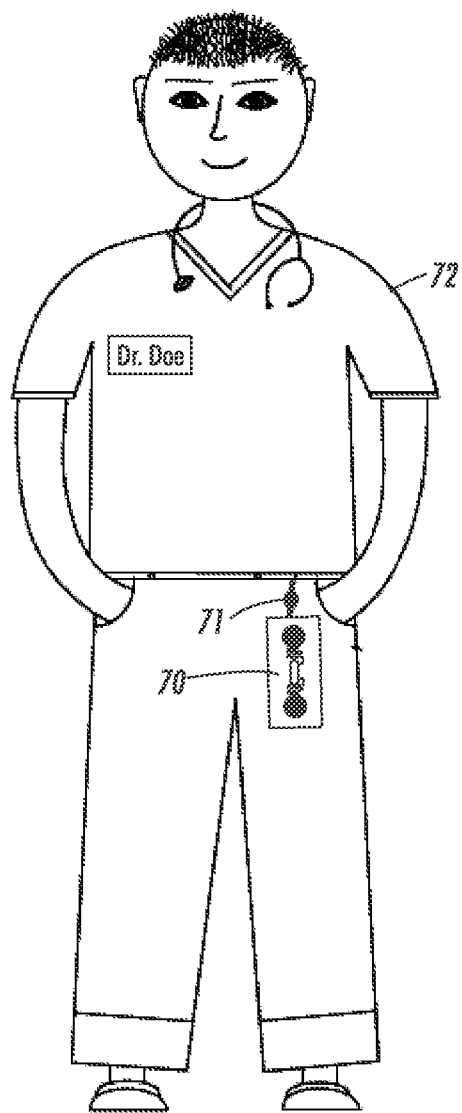
FIG. 5 is a block diagram showing, by way of example, a tracker on a clip.

In contrast to patients, hospital employees are generally at the hospital on a regular, long-term basis, and more permanent and potentially more expensive trackers can be issued to the employees for use during employment by the hospital. Conventionally, employees are issued an identification badge for identification verification by patients and for access into restricted areas. The trackers can be printed on, embedded in, or affixed to the badges, which are worn by the employees. FIG. 4 is a block diagram showing, by way of example, a tracker 61 on a lanyard 62. Specifically, the tracker 61 can be combined with an identification badge, which a hospital employee 62, such as a doctor or nurse, can wear around his neck via a lanyard 62. Alternatively, the employee may prefer to wear the badge clipped to his pocket or to the waistband of his pants. FIG. 5 is a block diagram showing, by way of example, a tracker 70 hooked on a clip 71. The clip 71 can be attached to a pocket or waist band of the employee 72 and hold the badge to which the tracker 70 is embedded, printed on, or affixed.

Figure 6:
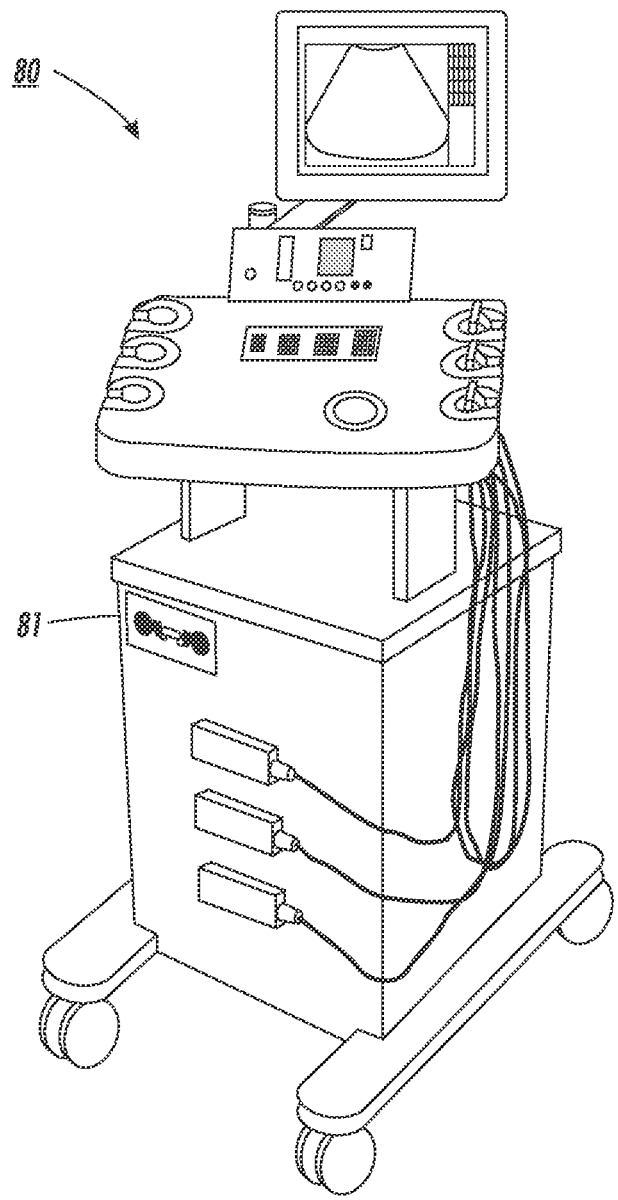
FIG. 6 is a block diagram showing, by way of example, a piece of medical equipment with a tracker.

In addition to individuals, a tracker can be used to monitor equipment. FIG. 6 is a block diagram showing, by way of example, a piece of medical equipment 80 with a tracker 81. The tracker can be removably affixed to the equipment via adhesive, such as glue or rubber, or by hook and loop material. Alternatively, the tracker 81 can be embedded into the equipment, or printed or embossed directly on the equipment. As the equipment 80 moves throughout the hospital, reader systems can identify the tracker. The location of the tracker 81 is then determined based on the particular reader systems that identified the tracker during a common interrogation, a location of the reader systems that identified the tracker, and a reading range of those reader systems.

Figure 7:
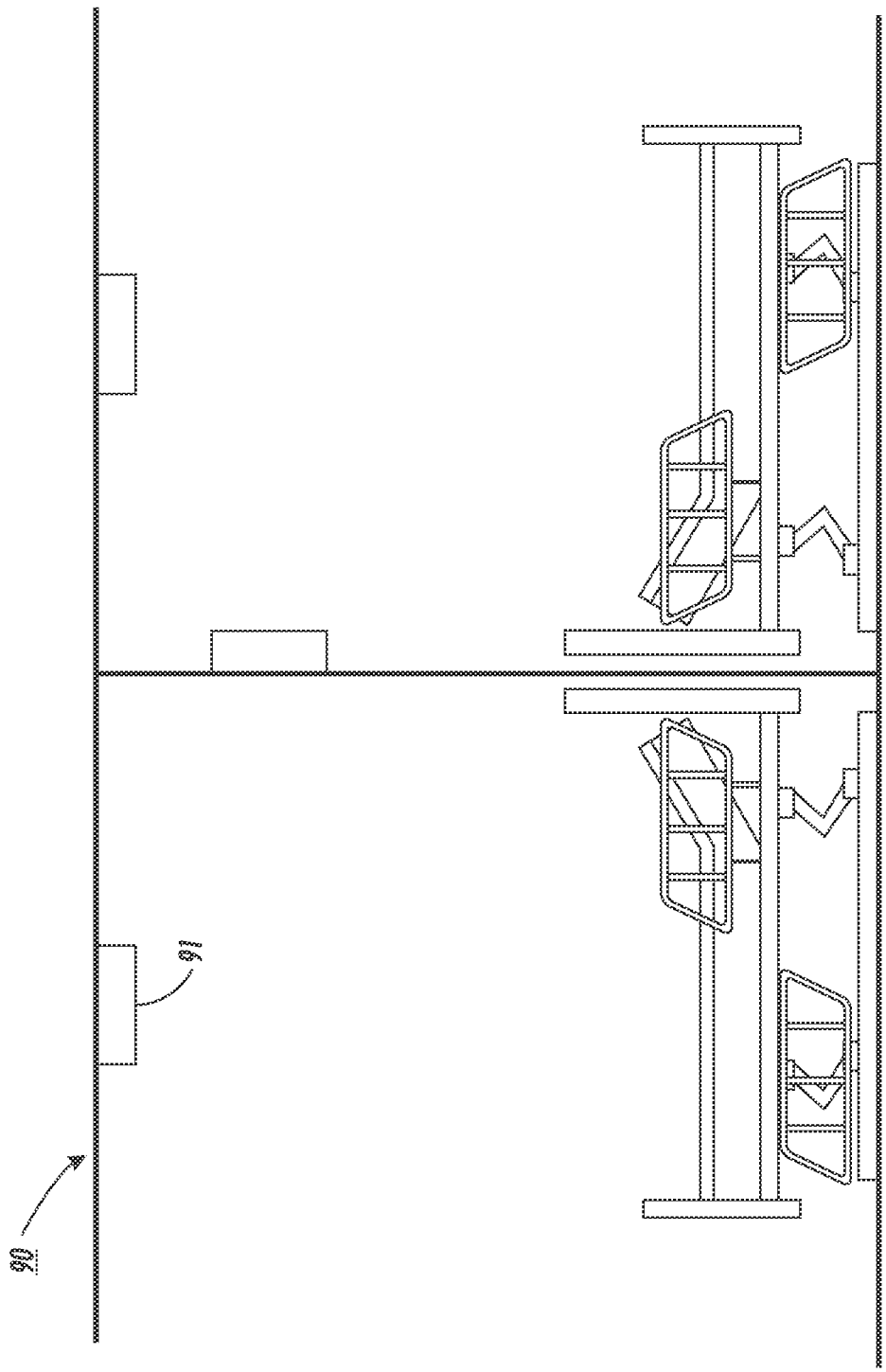
FIG. 7 is a block diagram showing, by way of example, a hospital room with tracker readers.

The reader systems can be systematically positioned in the hospital such that a tracker moving throughout the building is visible to one or more of the reader systems. FIG. 7 is a block diagram showing, by way of example, hospital rooms 90 with multiple reader systems. The hospital can include a plurality of reader systems 91 to identify the trackers and determine a location of each tracker. Each reader system can include at least one antenna and a reader. An antenna identifies the trackers within a particular range of the reader system 91, while the reader processes identification information of the tracker. In one embodiment, the antenna and reader can both be positioned on a ceiling of the hospital, as well as on a post or wall within the hospital. In a further embodiment, the antenna and the reader can be separately positioned (not shown). For example, the antenna can be located on a ceiling, while the reader is placed on or within a wall.

Placement of the trackers on an entity, as well as placement of the reader systems in the hospital should be considered together since a communication path between the antennas and the trackers, within a particular range, is required. In one example, communication between the trackers and reader systems occurs via an unimpeded radio frequency communication. However, other types of communication are possible.

Figure 8:
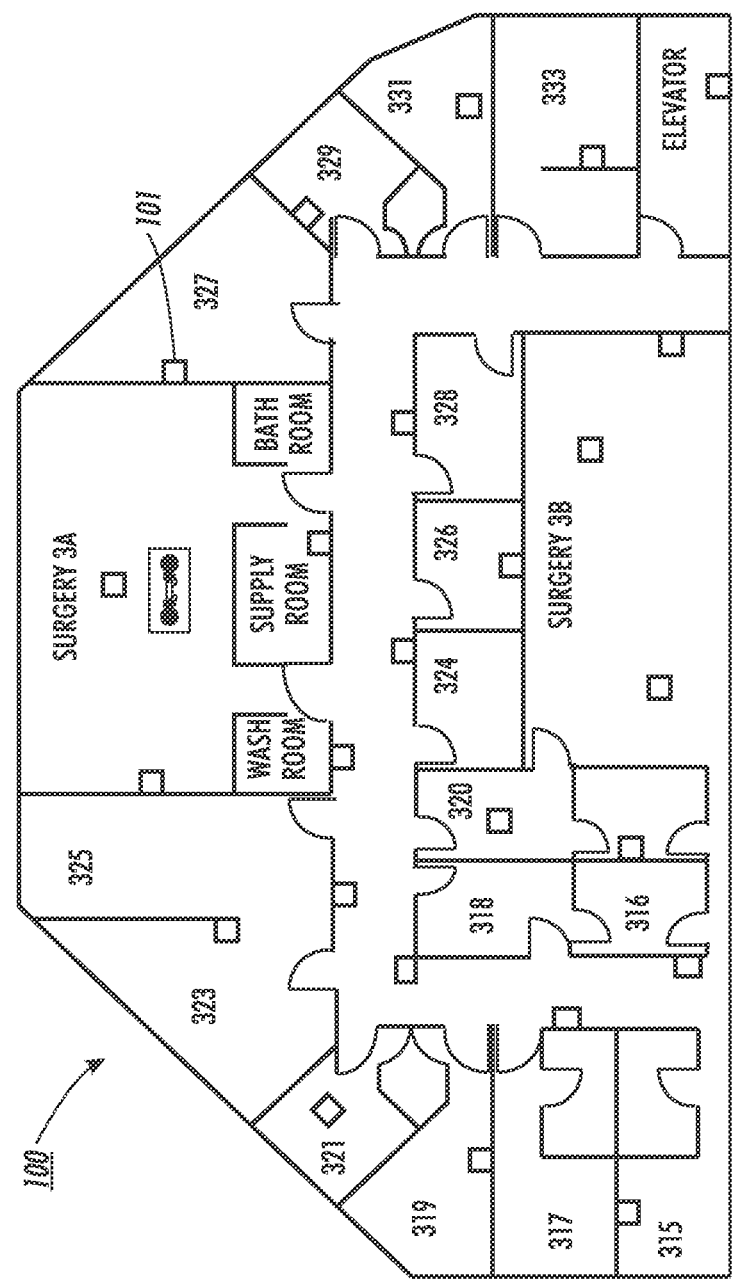
FIG. 8 is a block diagram showing, by way of example, a floor plan of a hospital with multiple reader systems.

Placement of the reader systems with respect to other reader systems should also be considered. For instance, a location of a tracker can be based on triangulation when three reader systems each identify a common tracker. Based on the location of the reader systems that identify the tracker and a known reading range of the reader systems, a general location of the tracker can be determined. FIG. 8 is a block diagram showing, by way of example, a floor plan 100 of a hospital with multiple reader systems 101. The reader systems 101 can be positioned within the hospital such that each tracker is in view of at least three reader systems; however, other numbers of reader systems are possible. In this example, the reader systems are located throughout the hospital floor, including in the hallways, patient rooms, surgery room, and equipment rooms, as well as in other locations on the floor. The reader systems 101 each identify trackers within a predetermined range. The location and range of those reader systems that identify a common tracker are then used to determine the tracker location. Other methods for determining tracker location are possible and may require a different configuration of the tracker reader systems.

Figure 9:
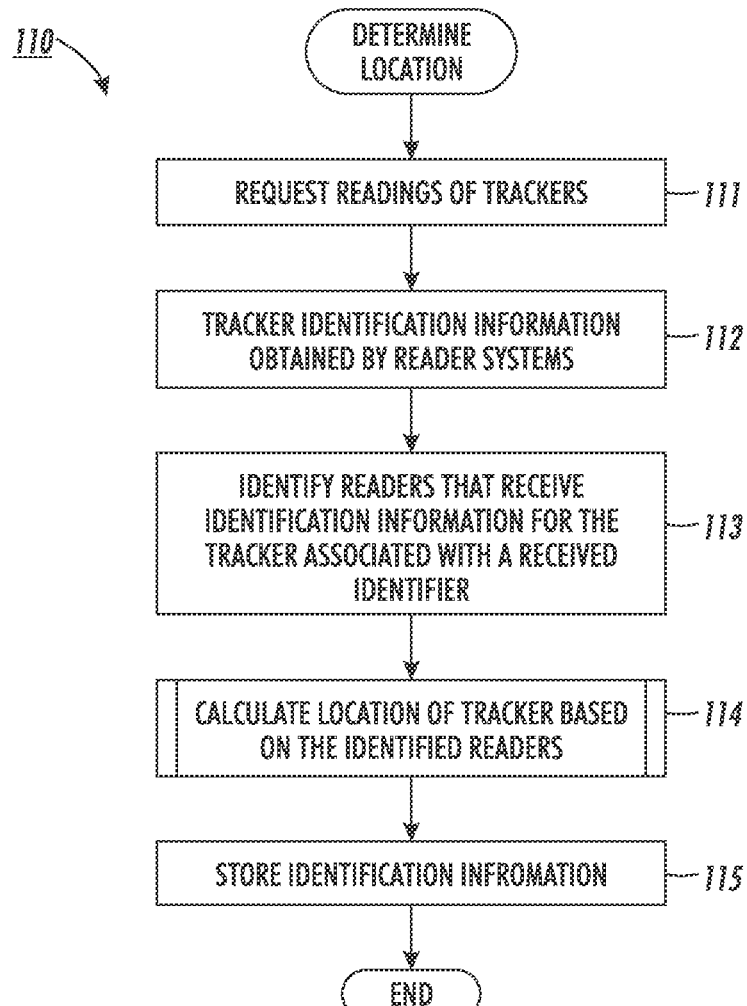
FIG. 9 is a flow diagram showing, by way of example, a process for determining entity location.

Determining the location of a tracker can require identification of the tracker by one or more reader systems. FIG. 9 is a flow diagram showing, by way of example, a process 110 for calculating a location of a tracker using identification information of multiple reader systems. On a periodic, continuous, or as-requested basis, readings of the trackers are requested (step 111) and tracker identification information is obtained (step 112) by the reader systems. Those reader systems that receive identification information for a common tracker are identified (step 113). The location of the tracker is calculated (step 114) based on a location of the reader systems that identify the tracker and on an overlap zone determined by the known reading ranges of those reader systems. In one embodiment, triangulation can be used to determine the location. The determined location is then stored (step 115) for the tracker and the entity associated with the tracker.

Figure 10:
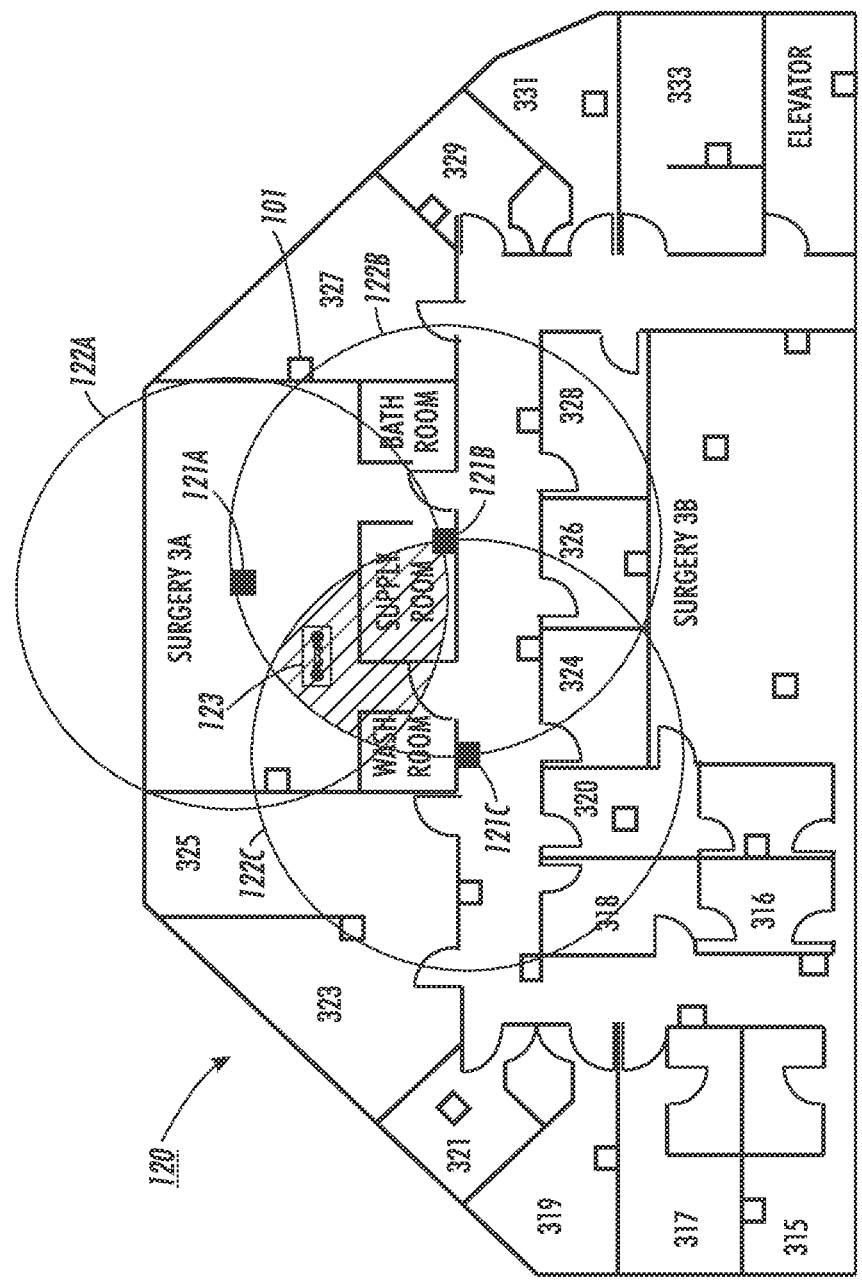
FIG. 10 is a block diagram showing, by way of example, a floor plan of a hospital with an identified entity.

Using triangulation, the location of an entity is calculated based on data from at least three reader systems with overlapping ranges. FIG. 10 is a block diagram showing, by way of example, a hospital floor 120 with multiple reader systems 121*a-c* identifying a tracker. The reader systems 121*a-c* are installed, for example, on the ceiling of the floor, and those reader systems with a shorter reading range are positioned closer together than reader systems with a longer reading range so that the range of at least three reader systems overlap, which can represent identification of a common tracker by each of the overlapping reader systems.

In this specific example, three reader systems 121*a-c* are located in or near surgery room 3A on the West wing of Floor 3. One reader system 121*a* is located in the middle of the surgery room, a second reader system 121*b* is located in a supply room within the surgery room, and a third reader system 121*c* is located outside a wash room, in the surgery room. Each of the reader systems 121*a-c* has a common reading range that is designated by a circle 122*a-c* around the reader system 121*a-c*. Other reader systems with varying ranges can also be positioned throughout the hospital floor to identify trackers, as further discussed below with respect to FIGS. 11 and 12. Moreover, as mentioned previously, the reader ranges need not be fixed, but can be varied by modulating the radio frequency power transmitted via the reader antenna, thereby enabling coverage of a larger area using fewer reader systems.

In this example, the reader systems 121*a-c* each have a reading range 122*a-c* that covers an area with a 16 foot radius. Meanwhile, surgery room 3A is about 32 feet long by 28 feet wide. Other room sizes, reading ranges, and reader system locations are possible. During an interrogation, each of the reader systems 121*a-c* requests readings from trackers within range of that reader system. The readings can include identification of a tracker located on an entity that is within range of that reader system. For example, each of the three reader systems 121*a-c* described above obtain readings from a common tracker 123 that can be identified by a tracker number, name, or other identifier. A general location of the tracker 123 can be represented by identifying an area that is defined by overlapping reading ranges of the three reader systems. The location designated by the overlapping reading ranges can be calculated based on the location of the reading systems and the ranges of the reading systems using triangulation.

Figure 11:
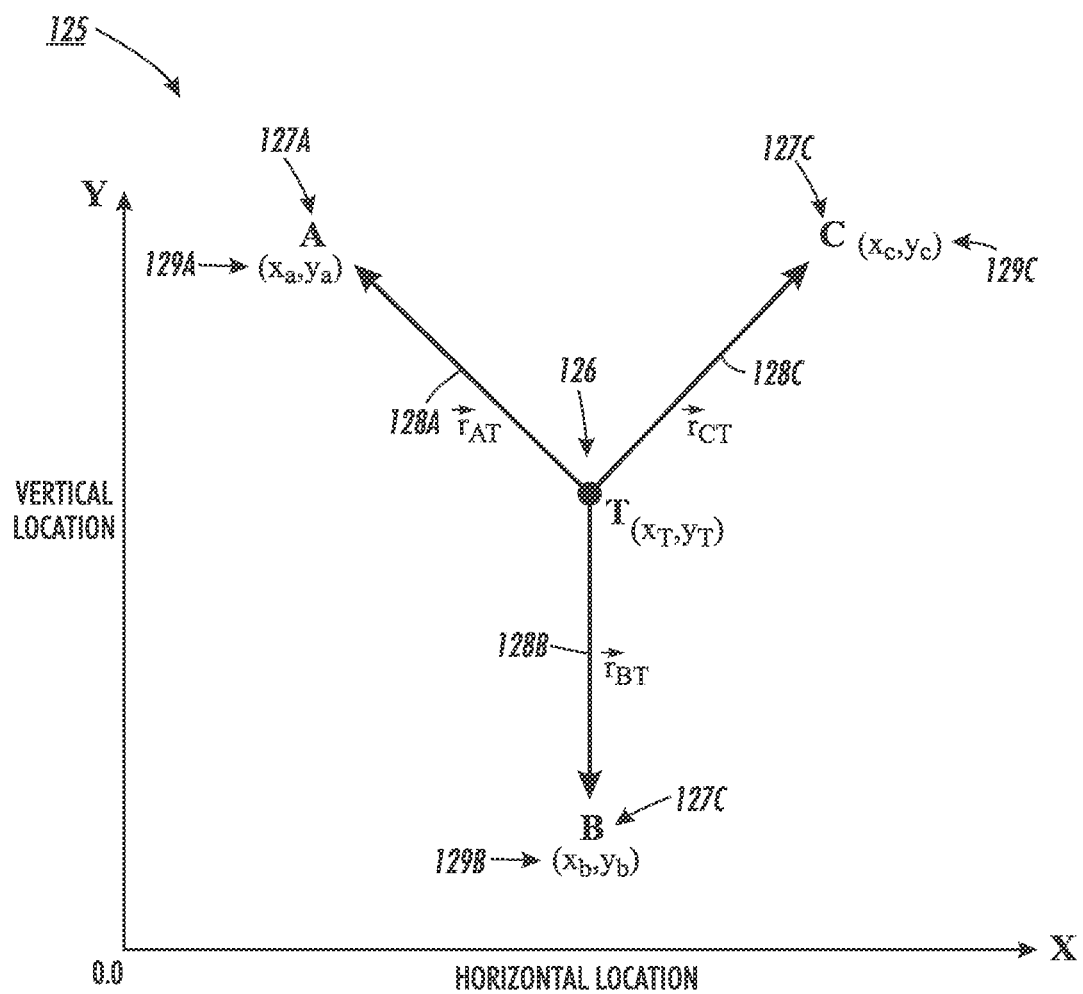
FIG. 11 is a block diagram showing, by way of example, a graph of a tracker within range of three reader systems.

The location of the tracker can be determined using known locations of the reader systems that identify the tracker and a signal strength from the tracker to each of the reader systems. FIG. 11 is a block diagram showing, by way of example, a graph 25 of a tracker 126 within range of three reader systems 127a-c. Each of the reader systems A 127a, B 127b and C 127c is associated with a known location coordinate represented by (x,y) 129a-c, while a location of a tracker (T) 126 is unknown. However, the location of the tracker 126 can be determined based on the known location coordinates 129a-c of the reader systems 127a-c that identify the tracker 126 and a distance of each reader system from the tracker. The distances of the reader systems from the tracker can be determined based on signal strength.

Specifically, a vector 128a-c from the tracker 126 to each of the reader systems 127a-c is formed, with a direction of the vector 128a-c extending from the tracker 126 to the respective reader systems 127a-c. Each vector equals the distance between the tracker and the respective reader system. For instance, the vector for reader system A is represented as $|\vec{r}_{AT}|$ 128a, the vector for reader system B is represented as $|\vec{r}_{BT}|$ 128b, and the vector for reader system C is represented as $|\vec{r}_{CT}|$ 128c. Prior to calibration, each vector distance can be represented by a signal strength, $S_A$, $S_B$, and $S_C$ of each of the reader systems. Upon calibration, the coordinates of the tracker 126 can be determined using the known distances of each reader system 127a-c from the tracker 126 based on the signal strength and the known coordinates of the reader systems 127a-c using the following equations:

$$Y_T = \frac{(x_A - x_B)[x_c^2 + y_c^2 - x_B^2 - y_B^2 + \beta - \gamma] +}{2[(x_B - x_c)(y_A - y_B) - (x_A - x_B)(y_B - y_c)]} \quad (1)$$

$$X_T = \frac{x_A^2 - x_B^2 - (\alpha - \beta) + (y_A - y_B)(y_A + y_B - 2y_T)}{2(x_A - x_B)} \quad (2)$$

Each of the known distances $|\vec{r}_{AT}|$ 128a, $|\vec{r}_{BT}|$ 128b, $|\vec{r}_{CT}|$ 128c, can be denoted by $\sqrt{\alpha}$, $\sqrt{\beta}$, and $\sqrt{\gamma}$ respectively. Therefore, $\alpha$ is represented by $|\vec{r}_{AT}|^2$, which is a known value based on the signal strength of the tracker to the reader system A, $\beta$ is represented by $|\vec{r}_{BT}|^2$, which is a known value based on the signal strength of the tracker to the reader system B, and $\gamma$ is represented by $|\vec{r}_{CT}|^2$, which is a known value based on the signal strength of the tracker to the reader system C. Meanwhile, the x and y coefficients are known location coordinates for each of the reader systems A 127a, B 127b, and C 127c.

Once determined, the location of the tracker 123 can then be provided to a user that requested a location of an entity associated with the tracker 123. Identifying an entity's approximate location, such as within a particular area of the hospital can be sufficient since the user can locate the entity quickly. In the above example, the user was able to identify the entity associated with the tracker as being in Surgery 3A room on Floor 3 in the West wing. More specifically, the tracker was identified as being in either the main surgery room, the wash room, or the supply room, but not the bathroom. The location can be provided to the user as one or more room numbers, room names, or as a designated section or area of the hospital.

Figure 12:
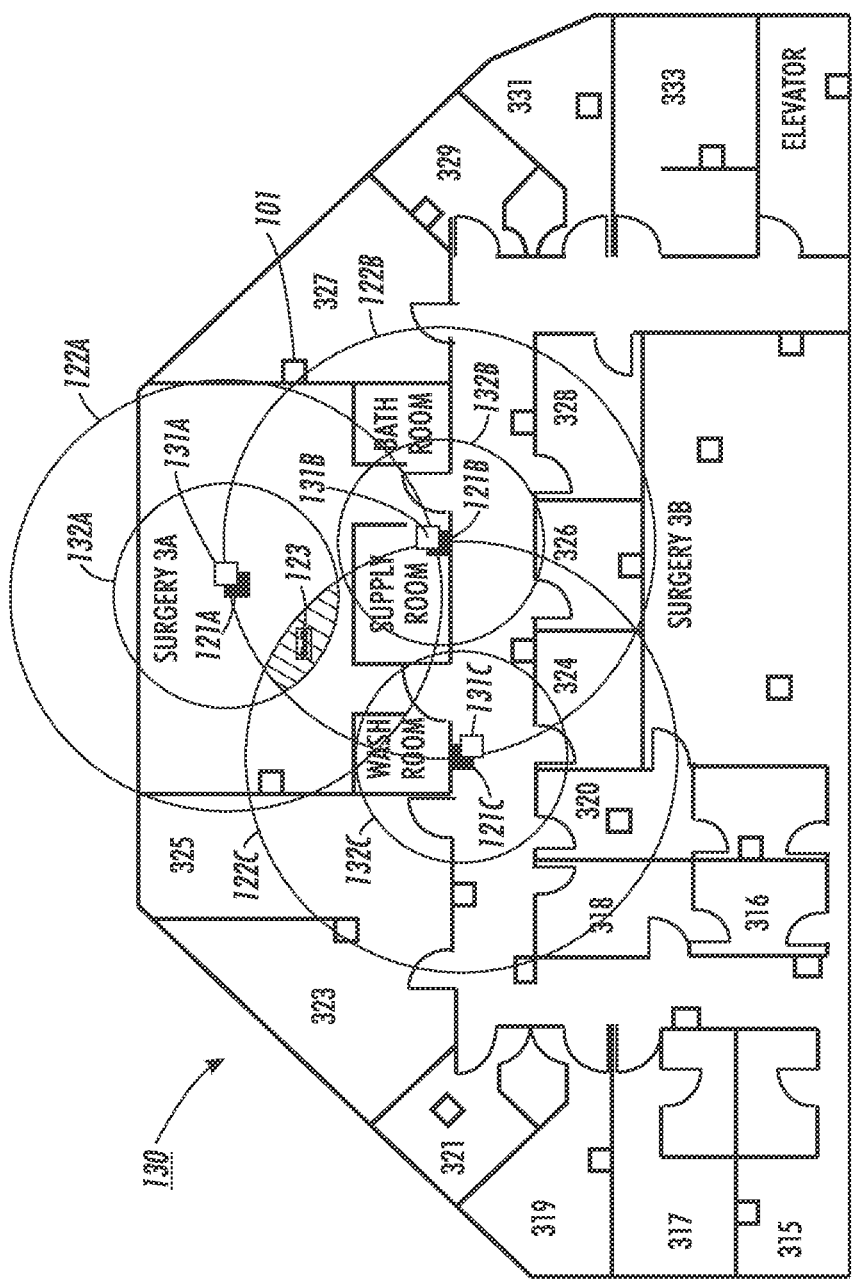
FIG. 12 is a block diagram showing, by way of example, a floor plan of a hospital with multiple reader systems of various ranges.

Location accuracy can vary based on the types of reader systems, the locations of the reader systems, and the ranges of the reader systems. For example, reader systems of various ranges can be used to broaden or refine a location determined for an entity. FIG. 12 is a block diagram showing, by way of example, a hospital floor 130 with multiple reader systems of various ranges identifying a tracker 123. Two or more reader systems of varying ranges can be placed together to determine a location of an entity. For example, a shorter range 131a-c reader system is positioned adjacent to each of the reader systems of FIG. 10. Three longer range 122a-c reader systems 121a-c each identify the tracker 123, as well as a reader system 131a with a shorter range 132a. Based on the reader systems that identified the tracker, an area in which the tracker is located is identified by an overlapping range area of each of the four reader systems. The actual location of the area can be determined, for example, by triangulation. In comparison with the reader system arrangement provided in FIG. 10, the reader system configuration of the FIG. 12 narrows the location that the user has to look for the entity.

Figure 13:
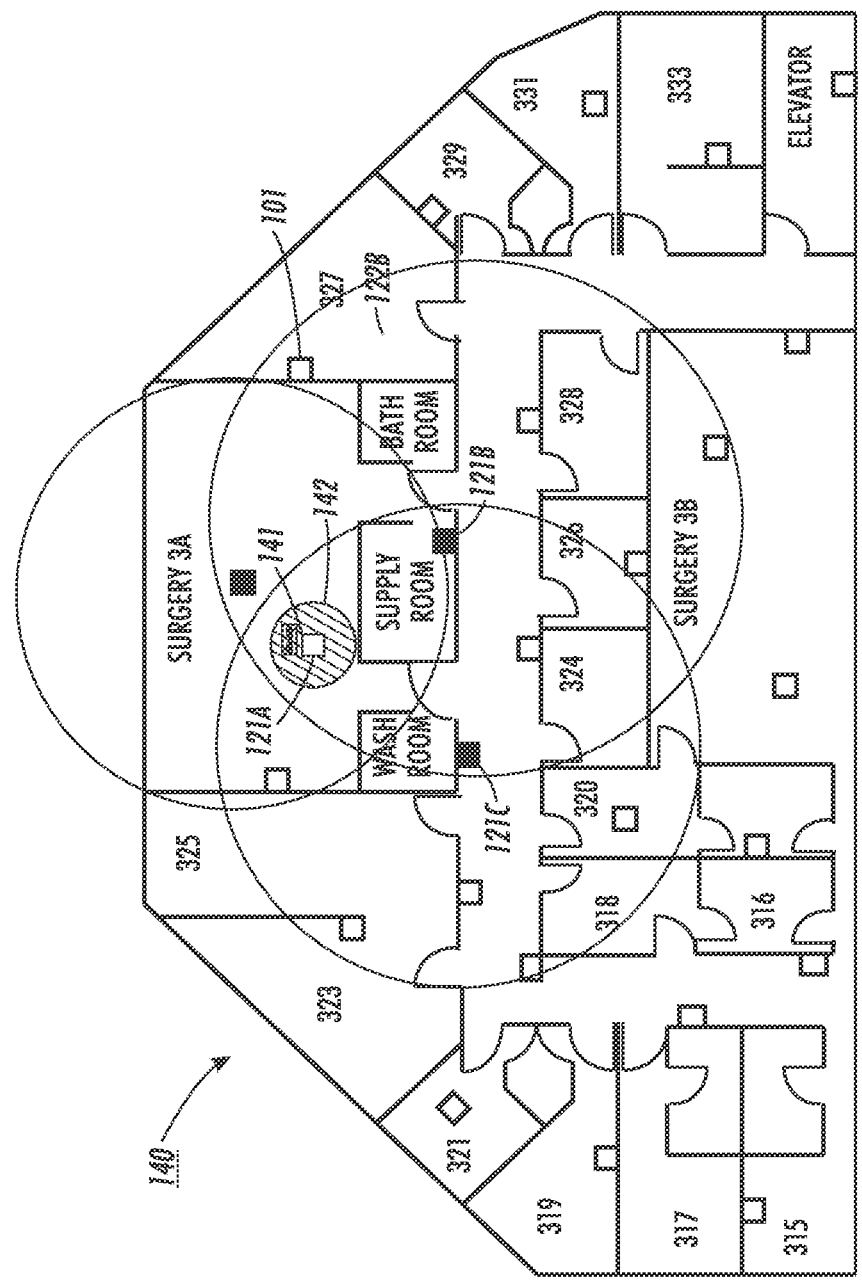
FIG. 13 is a block diagram showing, by way of example, a floor plan of a hospital with multiple reader systems of various ranges, in a further configuration.

In a further configuration, shorter-range reader systems can be interspersed with longer-range reader systems. FIG. 13 is a block diagram showing, by way of example, a hospital floor with multiple reader systems of various ranges in a further configuration. For instance, a short-range 142 reader system 141 can be located on a ceiling of Surgery room 3A, just outside the supply room. Use of the short-range 142 reader system 141 in this example, can refine the location results provided by the example discussed above with reference to FIG. 10, which includes identification of the tracker in one of the main surgery room, wash room, or supply room. Adding the short-range 142 reader device 141 to the three long-range reader devices 121a-c described in FIG. 10 narrows the location of the entity to the main Surgery room 3A, as determined by the overlapping range areas of the four reader systems. The location defined by the overlapping range area can be determined via conventional methods, such as triangulation, and subsequently provided to the user.

Alternatively, RFID reader systems with programmable polling ranges provide additional flexibility for electronically reconfiguring the locator system grid without physically relocating the reader systems. Such dynamic reconfiguration could be used for improving the location accuracy of specific trackers and also to compensate for variations in the signal range caused due to building elements such as walls, structural beams, large metal objects such as fans and air conditioning system enclosures.

In a further embodiment, a single reader system can be positioned within each room in the hospital and the location of the tracker can be determined via the single reader system associated with the room in which the entity is located. Other configurations of the reader systems are possible.

The reader systems can obtain tracker readings to determine entity location on a regular, continuous, or periodic basis. As described above, the tracker readings for each tracker can include one or more tracker identities within range of each reader. Alternatively, if no trackers are located within the range of a particular reader, no readings are obtained or a negative reading may be provided. The tracker readings can be combined with reader information, including, a location of the reader and a range of the reader, as entity data. Subsequently, the entity data is combined with entity data from other readers that detected the same tracker to determine a location of the tracker and the entity associated with the tracker. In one example, the readers are positioned such that any location within the hospital is within range of at least three reader systems so that triangulation can be used to determine the tracker's location. However, different numbers and ranges of readers can be used, as well as different methods for determining location. Once determined, the locations associated with an entity are stored in a database for access by a user.

Figure 14:
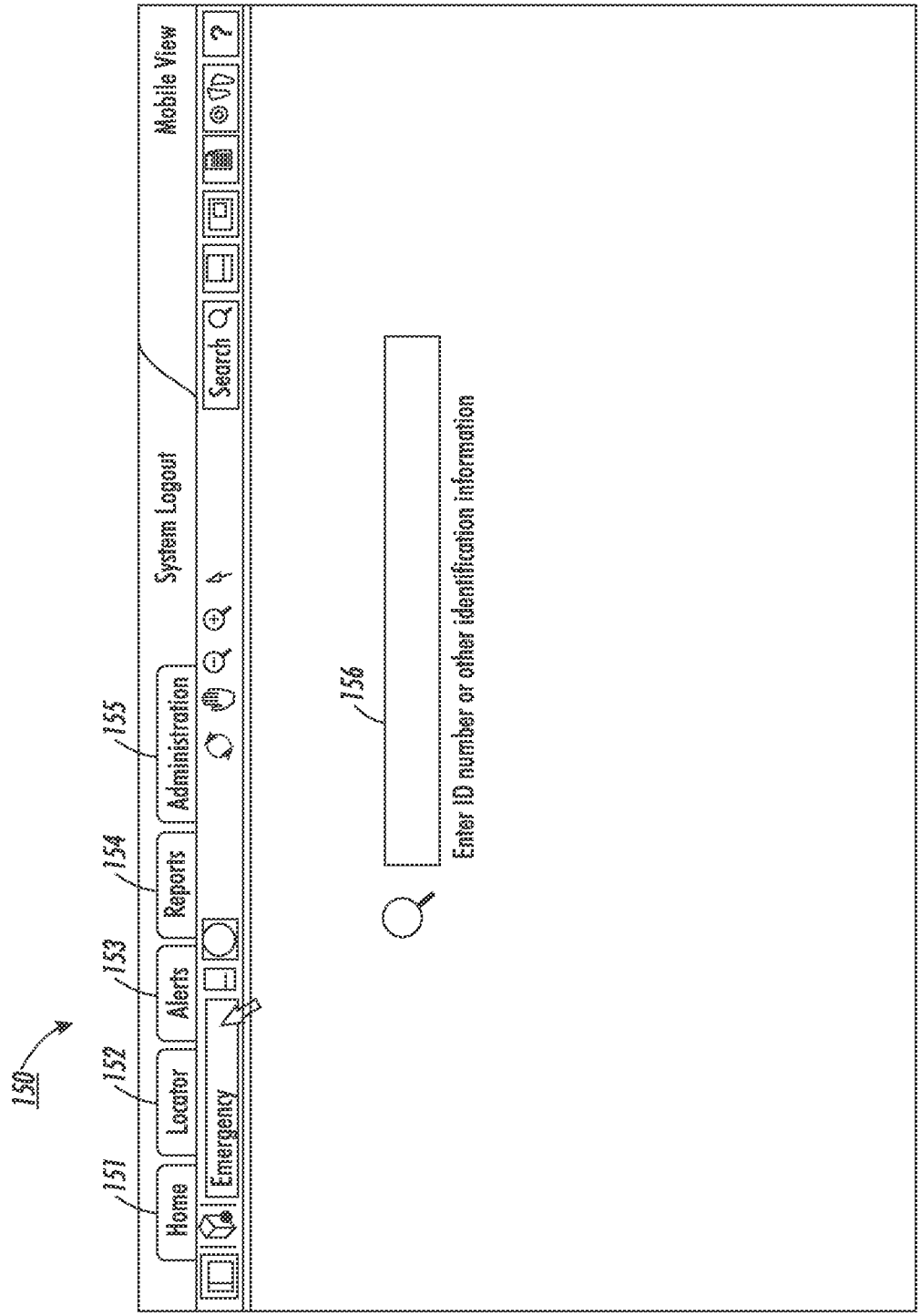
FIG. 14 is a block diagram showing, by way of example, a Web page for searching for an entity location.

The user can access the entity locations via a user interface, such as a Website. FIG. 14 is a block diagram showing, by way of example, a Search Website 150 for searching for an entity location. The Website can include a home tab 151, a locator tab 152, an alert tab 153, a report tab 154, and an administration tab 155, as well as other tabs. A Web page associated with the home tab 151 can include the hospital name and login information for the user, including user name and password. In one embodiment, only those users who are registered and authorized to conduct an entity search will be allowed to access the tabs, other than the home tab. Further, an access list can be maintained to identify those entities for which a particular user is able to access location information. For instance, a visitor may only be able to access administrative medical personnel, while a nurse is able to access all employees and equipment within the hospital. The access list can include an identity of each registered user and a list of entities for whom the registered user is able access locations.

After the user has been validated by his user name and password, the user can conduct a search for a particular entity using the locator tab 152. The Web page associated with the locator tab 152 can include a search field 156 for the user to enter an identity of the entity whose location is to be determined. The identity can include a name, make, model, or other identifier. In one example, Dr. Smith is required to perform an emergency surgery on a patient in room 232 on the second floor of the North wing and is not responding to calls over the intercom. At 2:50 p.m., Nurse Leslie logs into the Search Website 150 via the home tab 151 and accesses the search field 156 via the locator tab 152. Nurse Leslie enters the words "Julie Smith" into the search field and subsequently selects an "enter" or "search button (not shown) to conduct the search.

During the search, the entity identifier entered by the user is compared with a database of entities to determine the entity associated with the identifier. Subsequently, a location of the entity can be determined upon the entity location request or can be obtained from the database. When the location is obtained from a database, the most recently determined location can be located, obtained, and provided to the user. Returning to the above example, Dr. Smith's location was determined every 15 minutes since she started her shift at noon. Thus, Dr. Smith's location was first located within the hospital at 12:15 p.m., since she was a little late, and again at 12:30, 12:45, 1:00, 1:15, 1:30, 1:45, 2:00, and 2:15 p.m. At 12:15 p.m., Dr. Smith was determined to be in the staff locker room on the first floor of the hospital in the South wing. At 12:30 p.m., Dr. Smith was determined to be in the hallway outside of room 333 on Floor 3 of the West wing. At, 12:45 p.m., Dr. Smith was located in the wash room on the third floor of the West wing preparing for a surgery. At 1:00, 1:15, 1:30, 1:45, 2:00, and 2:15 p.m., Dr. Smith was located in surgery room 3A on the third floor of the West wing performing an appendectomy.

Nurse Leslie requested the location of Dr. Smith at 2:50 p.m. The most current location, in surgery room 3A, obtained for Dr. Smith at 2:45 p.m. can be provided to the requesting user as Dr. Smith's current location. Alternatively, the location can be newly obtained at the time of the request. For instance, a request for tracker readings can be transmitted to the reader systems on an 'on-demand' basis and a new location of Dr. Smith can be determined and provided to nurse Leslie upon request.

When the user enters the identification information for the entity in the search field, the user can also select whether he wishes to obtain the most recently determined location or a newly determined location. Alternatively, the hospital can make the determination as to providing the most recently determined location or a newly determined location depending on the urgency of the request, for example, whether the location request is in relation to an emergency situation requiring a particular doctor or surgeon or whether the request is for a non-urgent matter. Further, a determination of which location, the most current or newly defined, can be determined based on a threshold. For instance, the most recently provided location can be provided when the time difference of the most recently provided location and time of request by the user satisfies a predetermined threshold.

Returning to the above example, the predetermined time threshold is six minutes. The time difference between the most recently determined location of Dr. Smith at 2:45 p.m. and Nurse Leslie's request at 2:50 p.m. is five minutes. Thus, the difference of five minutes is less than the six minute threshold so the most recently determined location of Dr. Smith will be provided to the user. If the time difference exceeds the threshold, a new location can be determined. Other thresholds can be used. However, the threshold should be small enough that the entity does not move too far from his most recently determined location, so the user can easily find the entity based on the most recently determined location.

Figure 15:
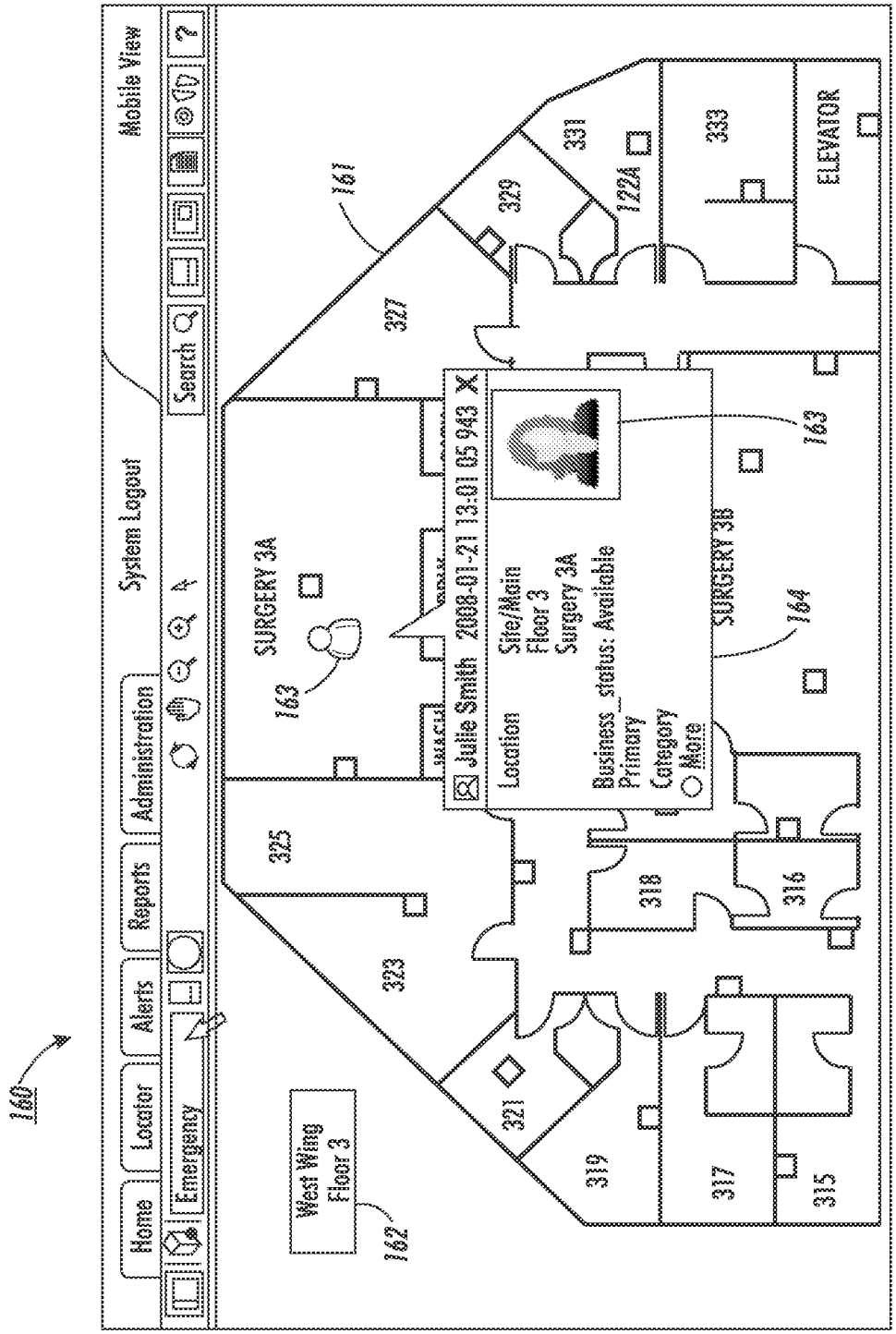
FIG. 15 is a block diagram showing, by way of example, a Web page of a map with an entity location.

Once determined, the location of Dr. Smith is provided to the requesting user and can include one or more of a room number or name, a floor number, or a wing of the hospital, as well as other location information. Alternatively, or in addition, the entity's location can be presented on a map. FIG. 15 is a block diagram showing, by way of example, a Web page 160 of a map 161 with an entity location 163. The map 161 can be provided as a pop-up window or as a separate Web page, such as under the locator tab or a separate tab. Other presentations of the map are also possible. The entity associated with the tracker whose location was determined can be represented by an icon, avatar, text box, or other representation.

Returning to the above example, the location of Dr. Smith is determined to be in surgery room 3A. An icon, representing Dr. Smith, is positioned on the map in the middle of surgery room 3A, where Dr. Smith is performing the appendectomy.

An entity box 164 can be presented with the entity representation and can include information about the entity. The entity information can include an identifier, location, job title, security access, campus or building, and availability status, such as available or occupied, as well as other information. Additionally, the entity box 164 can include a photograph or drawing 165, of the entity, which can be helpful if the user must physically locate the entity and has not previously encountered the entity.

Returning to the above example, Dr. Smith is needed to perform an emergency surgery. After Nurse Leslie enters Dr. Smith's name into the search field, Dr. Smith's location is determined to be surgery room 3A on floor 3 of the West wing. Subsequently, Nurse Leslie personally sends a message to Dr. Smith in the surgery room, such as a by a private intercom system or a direct line to the surgery room, or physically goes to the surgery room to request that Dr. Smith perform the emergency surgery.

Figure 16:
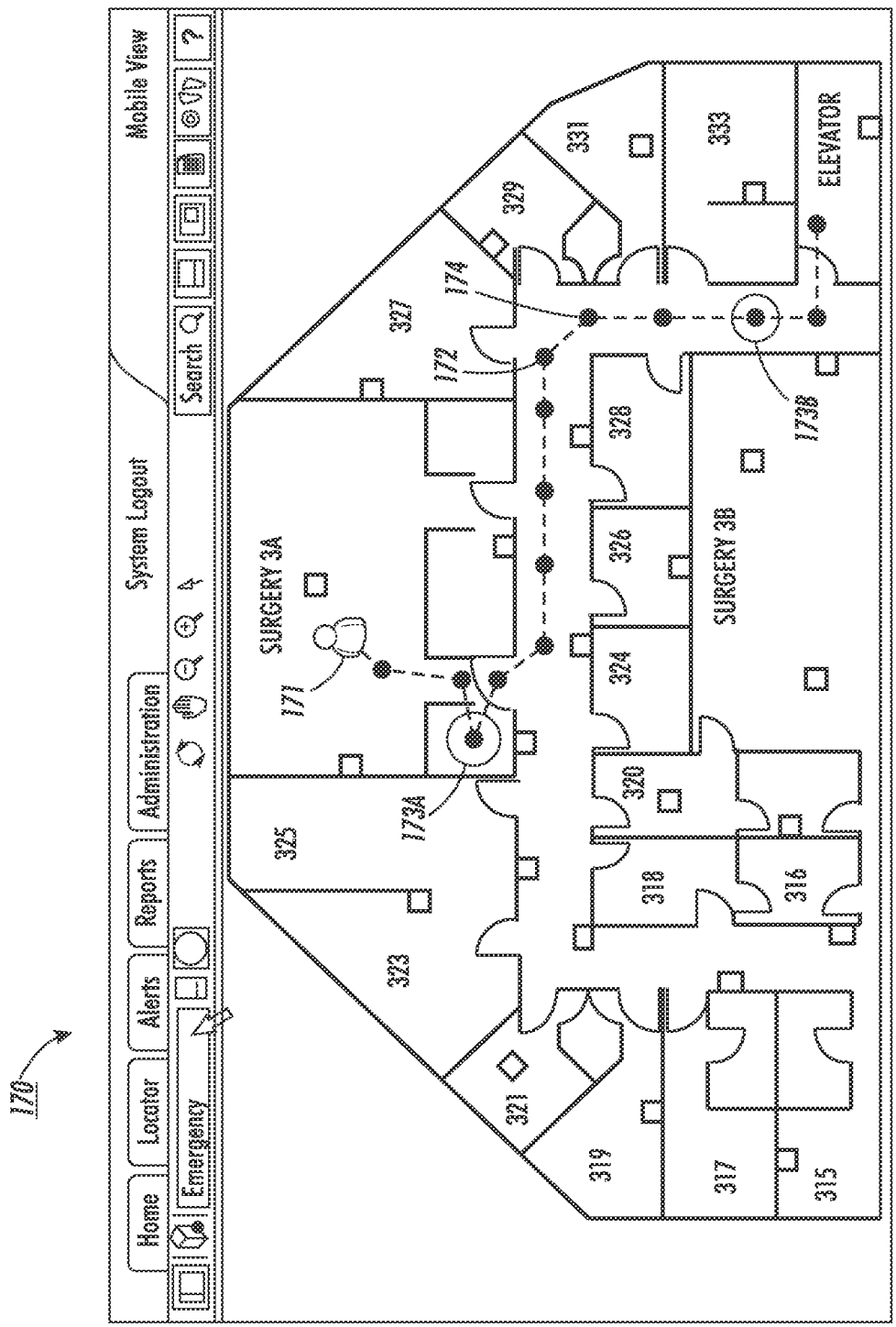
FIG. 16 is a block diagram showing, by way of example, a Web page of a map with a location history.

In addition to the entity location, a history of the entity's locations can be provided over a predetermined time period or a user-selected time period. The history can be provided as a list of times and locations or as a path on a map. FIG. 16 is a block diagram showing, by way of example, a Web page 170 of a map 171 with an entity path 172. A time period for the history is determined and the locations associated with times within the history time period are plotted on the map to create a path 172. The time period can be selected by the user or automatically determined. Additionally, information can be provided to the user to assist in selecting the time period. For instance, the entity's schedule can be provided so that the user can select a day, shift, week, or other time period for the entity's history.

The plotted locations 173a-b of the path 172 can be represented on the map by circles or other shapes. Subsequently, the path 172 of the entity can be filled in by further circles 174 or by drawing a line (not shown) through each of the circles. A larger circle around the plotted circles can distinguish the determined locations 173a-b from the circles that are used to fill in the entity's path. The representation 171 of the entity is displayed on the map at the most recently determined location to show the entity's current location.

Different history maps can be provided for different time periods or different area within the hospital. For example, a map can be displayed for each shift if the entity is a hospital employee. Also, if the entity moves between different floors or wings within the hospital, a different map of the area may be used. In some embodiments, a three-dimensional map can be used.

Alternatively, an entity history can be provided to a requesting user as a chart of times and locations. FIG. 17 is a block diagram showing, by way of example, a chart for an entity history. The chart can include entity information, such as an identifier, location, job title, security access, campus or building, and availability, such as available or occupied, as well as other information. Additionally, the chart includes a history of the entity, which is represented as a series of consecutive times and locations determined for the entity within a particular time range.

In one embodiment, the frequency of locations for inclusion of the history can be selected by the user. For instance, during a yearly inventory, a history is pulled for a particular ultrasound machine during the year 2013. Instead of returning times and locations for a time period of 15 minutes over the whole year, a single location can be provided for each day, for example. The location can be determined as the place where the equipment was located for the most time during that day or can be a new location, such as when the equipment was moved.

The location histories provide helpful information for tracking entities, such as a baby that has been taken from the maternity ward or a hospital visitor that has entered unauthorized areas. For example, areas where the baby is likely to be located can be stored with the tracker identification so that if a baby is determined to be outside one of the authorized areas, an alarm can sound to indicate the baby has been moved or taken. The location history can provide a path of the baby throughout the hospital and can be used to locate the track the baby. Also, the tracking of hospital staff can be used to automatically authenticate computer systems after detecting a presence of an authorized staff member so that appropriate data, such as patient data can be displayed when the staff member is present.

Further, the histories can be used to determine how long an entity has remained in one location. For example, a piece of equipment that has remained in a supply closet for over a year may need to be recalibrated. Additionally, a patient who is capable of movement may not have moved for a long period of time, which can indicate a fall. A time span during which the entity remained at the location can be determined by locating consecutive times associated with a common location and determining a time difference between the most recent time and the earliest time. The time that an entity spends at a common location can be shown on the map of FIG. 16, such as by a large dot or icon that gets larger the more time the entity spends at the location. In one embodiment, a threshold can be applied to the time span at the location. When the time span exceeds the threshold, an action can occur, such as an alarm sounding to indicate a possible patient fall or a need to calibrate a piece of equipment.

Additionally, the location history can be used with other data to determine whether the tracked entity has complied with a particular requirement or to determine performance of the entity, as described in further detail in commonly-owned U.S. patent application Publication No. 20150310508, pending, the disclosure of which is hereby incorporated by reference. For example, a location history of Dr. Smith can be obtained to determine physician effectiveness and efficiency. Subsequently, the patient schedule of Doctor Smith can be obtained. Together, the location history and patient schedule can be used to determine how much of Dr. Smith's time at the hospital was spent with patients and the average time that Dr. Smith spent with each patient by calculating time spent with patients using the location information, such as when Dr. Smith was determined to be in patient exams rooms, and the time at which the appointments were scheduled. Further, the location history can be used to determine whether an employee is working or taking a break. A break can be determined by identifying a location of an entity in the break room or by identifying the entity in an empty room or in non-patient rooms for a substantially long period of time.

The effectiveness of a doctor at treating patients can also be determined by comparing the location history with an outcome of patient visits. For example, Dr. Smith saw eight patients on Jan. 4, 2014. The first four patients were seen before lunch. The first patient came in for flu symptoms, the second and third patients came in for an annual exam, and the fourth patient had back problems. The amount of time spent with each patient can be obtained from the location history and when paired with patient outcome, can be used to determine whether Dr. Smith is more efficient and effective than other doctors based on the amount of time spent and whether the patient was adequately helped or correctly diagnosed.

In another example, the location history can be used to determine whether a person has washed or cleansed his/her hands prior to meeting or seeing a patient by determining whether the person entered a hand washing station or whether the person entity stopped in front of a hand sanitizing dispenser or station, and for how long the person remained at the hand washing station or sanitizing dispenser. A threshold can be applied to the amount of time spent at the station or dispenser to determine whether the person actually washed his hands. In one embodiment, the threshold can be at least 20 seconds. When the time spent at the station or dispenser exceeds the threshold, the person entity is determined to have washed her hands. However, if below, the person entity likely did not wash her hands for a sufficient amount of time or did not wash her hands at all.

The location histories can be used to identify actions for groups of entities, and make a determination whether an entity action is consistent with the group to which the entity belongs. For instance, patients who are immobile can be grouped together, as well as those patients that are partially mobile and fully mobile. The patients that are mobile, but remain in one location for an unusually long period of time may have fallen and cannot get up. To notify a caretaker, an alarm can sound when the usually mobile patient has remained in the same position for a threshold amount of time. Whereas, a person that is immobile is likely to remain in one location for long periods of time. In a further example, employees can be grouped into working and non-working entities to determine whether those entities that are clocked in are working.

Although the tracking of objects has been described above with reference to entities within a hospital, other objects can be tracked, such as individuals, including children, or things, such as cars, books, office or laboratory equipment, gym equipment, luggage, and toys, using related identifier-tracker pairs, as described in further detail in commonly-owned U.S. Patent Application Publication No. 20150309156, pending, the disclosure of which is hereby incorporated by reference. For instance, children can be tracked within a shopping mall so that if a parent accidentally becomes separated from her child, a current location and a path of the child can be determined, and the parent and child can be reunited. In this example, a ticket having an identifier and a tracker can be provided to the parent. The parent retains the identifier and removably affixes the tracker to the child, such as on a wristband or a shirt or hat of the child. Reader systems are positioned throughout the shopping mall and can take readings of trackers within a specified range on a periodic, continuous, or as-requested basis. The location of the tracker is calculated using data regarding the reader systems that identified that tracker and can be stored in a database. If the child becomes separated from the parent, the parent locates a console to scan the identifier. The tracker associated with the identifier is identified and the stored location of the tracker at one or more times can be provided to the parent to track a route of the child. Additionally, a further reading from the reader systems can be requested to identify a current position of the child so that the parent and child will be reunited.

Further, shopping habits of a consumer can be tracked within the shopping mall and can be used for directed advertising. For example, a retailer can affix a tracker to an item purchased by a consumer, while maintaining the identifier. Reader systems positioned throughout the mall can identify the tracker as the consumer moves throughout the shopping mall. Based on locations of the tracker, a retailer can identify the stores in which the consumer shopped to determine a specific style or preference of that consumer.

In a further embodiment, drivers can efficiently locate their parked vehicles using a parking locator system that employs a "smart" ticket having one or more functional sections, including an RFID transponder (tag) section and a paired identification section, as described in further detail in commonly-owned U.S. Patent Application Publication No. 20150309156, pending, the disclosure of which is hereby incorporated by reference. In some embodiments, the identification section can be a scannable QR code. In other embodiments, the identification section can be a bar code or a simple printed number. The identification section of the smart ticket identifies the specific RFID tag associated with the ticket, which can be issued to an individual vehicle when entering a parking structure. Before leaving a parked vehicle, a driver separates the two sections and leaves the RFID tag section on or in the vehicle, such as on the vehicle dashboard or window. The driver keeps the identification section of the ticket when exiting the vehicle. Upon the driver's return, the identification section is used to look up the associated RFID tag. The locator system described in this application then finds the vehicle containing the identified RFID tag and provides the location of the vehicle to the driver.

Further still, the tracker can store information regarding the object to be tracked or the individual tracking the item. For instance, cars can be tracked within a parking facility by placing the tracker in a parked car. A photograph of the parked vehicle can be taken as the vehicle enters the parking facility. Image processing can be performed on the photograph to determine a make, model, vehicle year, or license plate, which can be associated with the occupancy ticket. If the driver loses the retained identification portion of the occupancy ticket, the driver can enter the make, model, year, or license plate number of his vehicle to identify the tracker associated with that vehicle and the location of the tracker. Other information can be stored with the occupancy ticket, such as a time the driver entered the garage, which can be used to automatically determine payment due for the time the vehicle was parked in the facility. As well, frequent users of the garage, may associate a bank account or credit card with their vehicles so that the information can be linked to the tracker for automatic payment upon entering or exiting the garage.

In yet a further embodiment, a user can take a photograph of the identifier for later scanning if the user does not want to hold on to the identifier provided by a dispenser. Alternatively, a camera located at the entrance of the parking facility can take a picture of the user and apply facial recognition software and techniques to associate the user directly with the identifier. Then, the user may simply step in front of a console with a camera that can automatically recognize them and display the location of the vehicle.

To ensure that an entity can be accurately tracked, a network of reader systems, or nodes, must be strategically positioned throughout a structure in which the entity is to be tracked. The network of nodes can be configured by calculating a range of each node and determining spacing of the nodes based on the ranges so that each location within the structure is within range of at least one node. In a further example, the nodes are strategically placed by range so that each location in the structure is in the range of three separate nodes. However, just using range to configure the nodes is not always effective as most structures include walls and rooms with metal that can affect the node ranges.

To account for different materials and equipment in the structure that can affect range, the nodes can first be placed solely on range. Subsequently, an active tag can be used to sweep the building and map out the locations determined for the tag. The map can be used to determine how many nodes detect each location determined for the tag and to reconfigure the nodes. If more than three nodes have identified the tag at some locations, the nodes can be moved further away from each other to cover the structure using the least amount of nodes necessary so as to reduce cost. In contrast, if two or less than two nodes identify the tag, more nodes should be added within the structure to identify a location using triangulation. In a further embodiment, the location tracking system can include a programming mode in which an area of the structure is saturated with nodes. The area is swept with a tag and the system continuously turns off nodes to determine a minimum viable amount of nodes necessary for determining user location, such as through triangulation. Once the necessary nodes for the area have been determined, the configuration of nodes for a further area within the structure can be determined.

In yet a further embodiment, the nodes can be configured within an area and to ensure that each location in the area is in range with three or more nodes, the ranges of the nodes can be adjusted accordingly. Interrogation of the reader systems can depend of the type of object being tracked. For instance, readings may be collected more often, such as every minute, for individuals who move from location to location, than parked vehicles that do not move, for which readings can occur every five minutes. Other time periods are possible.

While the invention has been particularly shown and described as referenced to the embodiments thereof, those skilled in the art will understand that the foregoing and other changes in form and detail may be made therein without departing from the spirit and scope of the invention.

What is claimed is:

1. A computer-implemented system for obtaining entity location histories, comprising:
   a tracker associated with identification data for an individual comprising one of a health care professional or a patient within a hospital and placed with the individual via an adhesive, a lanyard, a wrist or leg band, or a clip;
   three or more reader systems that each receive location readings from the tracker in the hospital, wherein each reader system is positioned within the hospital; and
   a server to obtain real time locations of the individual by performing the following:
      receive the location readings and locate an overlapping interrogation zone comprising a region that is shared by reading ranges of the reader systems;
      receive a query for information about the individual comprising an identifier for the tracker associated with the individual;
      calculate the location of the tracker, comprising:
         determine a signal strength of the tracker to each of the reader systems; and
         determine coordinates YT and XT of the tracker based on a known location of each of the reader systems and the signal strengths to identify a precise location of the tracker within the overlapping region;
      store the location with a time stamp and other locations of the tracker and time stamps obtained over time;
      collect at least a portion of the locations from the central database for the tracker as a location history;
      determine from the location history an event comprising one of:
         an assessment that treatment provided by the individual is effective or not effective and whether a correct diagnosis was made by the individual; and
         an inference that the individual has fallen or the individual used a hand cleaning station when the location of the tracker is near the hand cleaning station; and
      trigger an alarm based on the determined event, wherein a recipient of the alarm addresses the event, in response to the query, to prevent detriment to health of the patient by recommending intervention of care of the patient by the health care professional to improve patient care.

2. A system according to claim 1, further comprising:
   a path determination module to determine a path of the patient from the location history; and
   a map module to map the path on a map.

3. A system according to claim 2, further comprising:
   a map showing a location of the patient via a symbol; and
   a symbol module to change a size of the symbol based on an amount of time the patient has spent at the represented location.

4. A system according to claim 1, further comprising:
   an accessibility module to associate with the tracker, at least one of areas of accessibility and restricted areas by the individual;
   an area determination module to determine that the individual is located in a restricted area; and
   an alarm sounded upon the determination that the individual is in the restricted area.

5. A system according to claim 1, wherein the location readings are obtained via one of RFID, ultrasound, Bluetooth, and infrared technology.

6. A system according to claim 1, further comprising:
   a tracking module to track groups of patients;
   a tag association module to associate the identification data of the patient with a category tag for the groups of patients to which the patient belongs;
   a location comparison module to compare the location history of the patient with those groups of patients with the associated category tags; and
   an analysis module to analyze actions determined from the location history of the patient in relation to actions associated with the groups of patients.

7. A computer-implemented method for obtaining patient location histories, comprising:
   associating a tracker with identification data for an individual comprising a health care professional or a patient within a hospital, wherein the tracker is placed with the individual via an adhesive, a lanyard, a wrist or leg band, or a clip;
   receiving a query for information about the individual comprising an identifier for the tracker associated with the individual;
   determining a real time location of the tracker for the individual, comprising:
      identifying three or more reader systems that receive location readings from the tracker in the hospital, wherein each reader system is positioned within the hospital;
      locating an overlapping interrogation zone comprising a region that is shared by reading ranges of the reader systems; and
      determining a location of the tracker, comprising:
         determining a signal strength of the tracker to each of the reader systems;
         determining coordinates YT and XT of the tracker based on a known location of each of the reader systems and the signal strengths to identify a precise location of the tracker within the overlapping region;
   storing on a central database, the location with a time stamp and other locations of the tracker and time stamps obtained over time;

collecting via a server at least a portion of the locations from the central database for the tracker as a location history;
determining via the server from the location history, an event comprising one of:
an assessment that treatment provided by the individual is effective or not effective and whether a correct diagnosis was made by the individual; and
an inference that the individual has fallen or the individual used a hand cleaning station when the location of the tracker is near the hand cleaning station; and
triggering an alarm based on the determined event, wherein a recipient of the alarm addresses the event, in response to the query, to prevent detriment to health of the patient by recommending intervention of care of the patient by the health care professional to improve patient care.

8. A method according to claim 7, further comprising:
determining a path of the patient from the location history; and
mapping the path on a map.

9. A method according to claim 8, further comprising:
representing a location of the patient on the map with a symbol; and
changing a size of the symbol based on an amount of time the patient has spent at the represented location.

10. A method according to claim 7, further comprising:
associating with the tracker, at least one of areas of accessibility and restricted areas by the individual;
determining that the individual is located in a restricted area; and
sounding an alarm upon the determination that the individual is in the restricted area.

11. A method according to claim 7, wherein the location readings are obtained via one of RFID, ultrasound, Bluetooth, and infrared technology.

12. A method according to claim 7, further comprising:
tracking groups of patients;
associating the identification data of the patient with a category tag for the groups of patients to which the patient belongs;
comparing the location history of the patient with those groups of patients with the associated category tags; and
analyzing actions determined from the location history of the patient in relation to actions associated with the groups of patients.

13. A method according to claim 7, further comprising:
configuring nodes that obtain the location readings of the tracker, comprising:
determining a range of each of the nodes;
positioning the nodes within a designated area based on the determined range; and
verifying a configuration of the nodes, comprising:
obtaining readings of an active tag at various locations within the designated area;
determining whether the tag is read by three of the nodes at each of the locations; and
reconfiguring the nodes such that each location in the designated area is within the range of at least three of the nodes comprising moving at least one of the more than three nodes within the designated area when more than three nodes read the tag and adding at least one more node to the designated area when less than three nodes read the tag.

14. A system according to claim 1, further comprising:
nodes that obtain the location readings of the tracker;
a range of each of the nodes, wherein the nodes are positioned within a designated area based on the determined range; and
an active tag to verify configuration of the nodes by obtaining readings of the active tag at various locations within the designated area, determining whether the tag is read by three of the nodes at each of the locations, and reconfiguring the nodes such that each location in the designated area is within the range of at least three of the nodes comprising moving at least one of the more than three nodes within the designated area when more than three nodes read the tag and adding at least one more node to the designated area when less than three nodes read the tag.

* * * * *